United States Patent [19]

Rothe et al.

[11] Patent Number: 4,604,264
[45] Date of Patent: Aug. 5, 1986

[54] TEST STRIPS

[75] Inventors: Anselm Rothe, Birkenau; Wolfgang-Reinhold Knappe, Bürstadt; Heinz-Friedrich Trasch, Ludwigshafen, all of Fed. Rep. of Germany

[73] Assignee: Boehringer Mannheim GmbH, Mannheim, Fed. Rep. of Germany

[21] Appl. No.: 560,916

[22] Filed: Dec. 13, 1983

[30] Foreign Application Priority Data

Dec. 23, 1982 [DE] Fed. Rep. of Germany ....... 3247608

[51] Int. Cl.⁴ ..................... G01N 21/78; G01N 33/52
[52] U.S. Cl. ...................................... 422/56; 422/57; 435/805
[58] Field of Search ..................... 422/55–58; 436/169, 170; 435/805

[56] References Cited

U.S. PATENT DOCUMENTS 3,802,842 4/1974 Lange et al. ............... 435/805 X
3,992,158 11/1976 Przybylowicz et al. ........... 422/57
4,292,272 9/1981 Kitajima et al. ..................... 422/57
4,477,575 10/1984 Vogel et al. ........................ 436/170

Primary Examiner—Arnold Turk
Attorney, Agent, or Firm—Felfe & Lynch

[57] ABSTRACT

A test strip has a reagent-containing film layer coating embedded at least preponderantly on and into only one side of a carrier layer made of a multifilar fabric or fleece.

12 Claims, 3 Drawing Figures

TEST STRIPS

The present invention is concerned with test strips and with a process for the production thereof.

Test papers, i.e. paper strips impregnated with reagents, have long been used in analytical chemistry for the detection of inorganic ions, organic substances and pH in liquids and gases. A further development is test strips or test rods in which the impregnated reagent paper is fixed to a synthetic resin film which serves as a handle. These are of increasing importance in analytical chemistry, such as in product control, in the investigation of water and effluent and especially in clinical chemistry in the investigation of body fluids. Hitherto, the reagents were usually impregnated into paper. Such test strips permit a rapid but only semi-quantitative visual determination by means of appropriate color-comparison fields. The natural non-uniformities of the papers and the non-uniform scattering of light thereby brought about make a quantitative, remission-photometric evaluation difficult.

With the need for quantitative-measurement results from test strips, e.g. in the case of blood and serum analysis, the use of reagent films has become increasingly common. The main advantage of these is the high degree of uniformity of the reagent layer. By means of the use of reagent films and of remission-photometric evaluation of the colour reaction, it is now possible to achieve with test strips measurement results with the quality of those obtained with wet chemical methods.

Examples of test strips based upon films are described in Federal Republic of Germany Patent Specification No. 15 98 153, for the determination of preferably glucose in blood, and in Federal Republic of Germany Patent Specification No. 31 18 381, in which is described a test strip construction for the determination of glucose in urine which permits the use of such a reagent film even in the case of unmeasured dipping into the sample liquid. Finally, in Federal Republic of Germany Patent Specification No. 31 30 749, there is described test strips for the determination of blood parameters which, in addition to the reagent zone, preferably based on a film, have a preceding erythrocyte separation by means of a glass fibre fleece and which permit an analysis directly from whole blood.

In the case of these test strips, the reagent film is either applied directly to the synthetic resin film serving as a handle or is present on an additional carrier film which imparts to it the stability necessary in the case of production and working up.

In the case of reagent films, which, in comparison with most cloth-like and "open" papers, have a smooth surface and only a small portion of hollow spaces, there are, however, to be found certain disadvantages precisely for these reasons.

Thus, in the case of test strips with a relatively closed or compact structure, such as are described in Federal Republic of Germany Patent Specification No. 31 30 749, difficulties can arise with an oxygen-consuming reaction in supplying sufficiently rapidly the oxygen necessary therefor in the required short reaction time. The reaction layers described therein are not in direct contact with the air but, from the very beginning, are closed off on their upper side by their oxygen-impermeable, transparent carrier film and also on their lower side by pressure of the reagent layer on a blood-separating fleece.

Therefore, in order to ensure a sufficient supply of oxygen, it is necessary, by laborious means in the measuring apparatus, to provide for a temporary lifting off again of the reagent layer from the separating fleece. In addition, this exerts an unfavourable influence on the quality of the measurement values.

Also in the case of the above-mentioned urine test strips according to Federal Republic of Germany Patent Specification No. 31 18 381, two phenomena arise which are to be attributed to the properties of the reagent films. In the case of these urine test strips for the determination of glucose, the reagent film is fixed to its carrier film over a slow-adsorbing paper by means of a thin covering mesh.

It has been shown that in the case of unskilled handling, an air bubble remains enclosed between the covering mesh and the surface of the reagent film which hinders a color reaction. Also, it can happen that, with adsorption of comparatively large amounts of excess urine into the slow-adsorbing paper, ugly colored edges appear which lead to incorrect interpretations of the results.

The air bubble formation could only be prevented by an expensive wetting agent treatment of the covering mesh and the colored-edge problem could only be solved by a limitation to small test zones.

Surprisingly, we have now found that the problems just mentioned can be overcome simply and completely when a reagent film is not coated on a solid carrier film, but on a carrier layer made of a multifilar fabric or fleece, preferably of polyester or polyamide.

Thus, according to the present invention, there is provided a test strip comprising a dry, reagent containing film layer coating embedded at least preponderantly onto and into only one side of a carrier layer made of a multifilar fabric or fleece.

Multifilar in the context of this application shall mean that the threads forming the fabric or fleece are themselves formed from a multitude of monofilar threads or fibres by spinning or twisting them, or from natural multifilar fibres like cotton.

For making this, a suspension or dispersion, preferably as concentrated as possible, of at least one synthetic resin, and possibly at least one reagent, pigment, and other filler or adjuvant material for the reagent film layer, in an appropriate solvent, preferably water, is applied with a rake or nozzle as a thin layer (20–500μ, preferably 50–200μ) to the fabric or fleece carrier layer and dried in such a manner as to obtain a dry film layer predominantly on one side of the carrier layer with a thickness of 10–200μ, preferably of 15–100μ.

It is a characteristic of the present invention that the coating mass remains on the upper side of the fabric whereas, depending upon the amount applied and mass properties, little coating mass gets into the interior of the fabric or on to its lower side.

Of course, other carriers or fabrics of other materials can also be used, for example cotton cloth, fleeces, papers and the like, so long as they satisfy the requirements with regard to uniformity, adsorptive ability, permeability and the like.

Monofilar fabrics, the embedding of which into coating masses has been described in Federal Republic of Germany Patent Specification No. 28 25 636, are not suitable for use according to the present invention. On the one hand, the coating mass penetrates through the fabric during the coating so that an additional carrier film must be used which is subsequently to be discarded.

On the other hand, in the case of monofilar fabrics, the accelerating effect in the case of oxygen-consuming reactions does not occur. Finally, uniform films are only possible with relatively high layer thicknesses and have an unacceptably long reaction time and also do not have the difference between the fabric side and the layer side which is typical of the present invention.

The reagents, film formers and adjuvant materials suitable for the construction of the reagent film are the same as those conventionally used for reagent films, such as are described, for example, in Federal Republic of Germany Patent Specifications Nos. 15 98 153; 29 10 134 and 31 18 381.

Suitable film formers are preferably organic synthetic resins, for example polyvinyl esters, polyvinyl acetate, polyacrylic esters, polymethacrylic esters, polyacrylamides, polyamides, polystyrenes, co-polymers, for example of butadiene and styrene or of maleic acid esters and vinyl acetate, cellulose and cellulose derivatives or gelatine. Other film-forming, natural and synthetic organic polymers, as well as mixtures thereof, can also be used, preferably in the form of aqueous dispersions. The film formers can also be dissolved in organic solvents, for example a co-polymer of vinyl chloride and vinyl propionate can be dissolved in ethyl acetate.

The reagents, pigments and other adjuvants necessary for the detection reaction are normally added directly to the dispersion. However, insofar as it is advantageous to do so, the formed film can also be impregnated with them. A preimpregnation of the added pigments with the reagents is also possible. The process can also be combined in that, for example, certain components are introduced into the dispersion and the others are subsequently impregnated on to the film. In this way, a certain spatial separation of the components can be achieved, which can result in more stable or more reactive tests. Furthermore, a separation can be achieved in that on to a first film layer there is applied a second film layer with a different composition.

Insofar as it is necessary, thickening agents, emulsifiers, dispersion agents, pigments, plasticisers, wetting agents and the like can also be added.

Dispersion agents, emulsifiers and thickening agents serve for the production and stabilisation of the dispersions. Pigments, for example titanium dioxide and silicon dioxide, improve the remission properties of films in that they provide for the smallest possible transparency and increased remission of the films. This is especially advantageous when the so-obtained diagnostic test agents are to be evaluated remission photometrically.

The properties of the film coating masses, as well as of the films, can be optimised with plasticisers. Thus, for example, their stability, their viscosity, their adhesion to the substrate to be coated and the like can be improved.

Wetting agents are added in order to achieve a better wetting of the film by the sample material. At the same time, they can also catalyse reactions or stabilise formulations or make the reaction colours more brilliant or of greater contrast.

The test strips described herein are preferably used for the detection of component materials of body fluids, such as urine, serum, faecal juices and saliva, but, with suitable modification, can also be used in other aqueous media, for example drinking water, effluent and the like, and possibly also in organic solvents in which they are insoluble.

The coated fabrics according to the present invention can be advantageously used in all cases where a film coated with a reagent film has previously been used. They are preferably used instead of the films in the devices according to Federal Republic of Germany Patent Specifications Nos. 31 18 381 and 31 30 749.

In the case of the devices according to Federal Republic of Germany Patent Specification No. 31 30 749, by the use of fabrics as substrates, there are, surprisingly, obtained more rapid reactions in the case of oxygen-consuming reactions, possibly because additional oxygen is made available due to the fabric structure. In the case of devices according to Federal Republic of Germany Patent Specification No. 31 18 381, a possible liquid supernatant flows off more quickly and without the formation of coloured edges. Also in the case of rapid dipping in or of insufficient wiping off, the contact between the reagent film and the covering mesh is so close that disturbing air bubbles can no longer be formed. The coated fabrics according to the invention can, of course, also be stuck or sealed directly on to synthetic resin films serving as handles but then, as in the case of test strips with conventional reagent films on carrier films, require a careful wiping off of excess test solution since this otherwise remains behind on the smooth surface as droplets and leads to spotty reactions. Underlaying with a slow adsorbing material does insofar not offer any advantages since the fluid only penetrates very slowly through the synthetic resin layer.

In comparison with test strips with impregnated paper, which are today still preponderantly used, the film-coated fabrics offer the following advantages:

due to the components of the coatings (colloidal thickening agents, dispersions) and the relatively low content of solvents in comparison with impregnation solutions, reagents which are incompatible with one another can remain stable in homogeneous solution for several hours in the presence of one another;

due to the use of pigmented coating masses, there can be achieved, for remission-photometric evaluation, a background with a degree of whiteness which cannot be achieved by impregnation of a paper;

in contradistinction to impregnated papers, in which the inhomogeneity of the paper disturbs a photometric evaluation, the coated fabric is homogeneous since the layer lies substantially on the upper side and has the same homogeneity as a film applied to another film. Shorter reaction times can thus be achieved since a thin film, compared with an adsorbent carrier (paper), is provided with only a fraction of the substrate, thus reacts quickly and practically the whole of the resultant reaction colour can contribute towards the measurement result. On the other hand, the possibility exists of a preceding reaction in that the fabric is, before the coating, impregnated with an additional reagent or the test solution is applied to the fabric and the reagent film via one or more adsorbent carriers.

The following exemplary preferred embodiments are described for the purpose of illustrating the present invention, but not limiting it, in conjunction with illustrations, in which.

EXAMPLE 1 SHOWN IN FIG. 1

Figure 1:
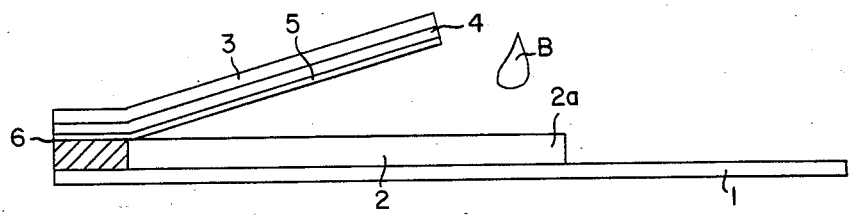
FIG. 1 is an elevation of one preferred embodiment.

Production of a test strip for the detection of glucose in blood

35 KU glucose oxidase
200 KU peroxidase
15 ml. 0.5M phosphate buffer, pH 5
0.3 g. sodium alginate
25 g. polyvinyl propionate dispersion in the form of a 50% dispersion in water
0.5 g. 3,3',5,5'-tetramethylbenzadine
0.2 g. phenyl semicarbazide
1 g. dioctyl sodium sulphosuccinate
6 ml. methoxyethanol
20 g. titanium dioxide
35 ml. water are worked up to give a homogeneous mass, coated with a thickness of 0.1 mm onto only one top side of a 150μ thick multifilar polyamide fabric (181 F 892 Schweizer Seidengaze-Fabrik) layer 5 and dried to form a reagent-containing film layer 4 embedded thereon. The coated fabric (4, 5) so obtained is thereafter attached to a transparent covering film layer 3 so that the covering film layer 3 lies over the reagent containing film layer 4. Subsequently, only one edge of a 1 cm. wide strip of this covered coated fabric (3, 4, 5) is fixed to a plastic strip 1 with a hinge 6, for example of adhesive, with the fabric layer 5 adjacent the plastic strip 1 in the manner illustrated in FIG. 1. A 15 mm. wide glass fiber fleece 2 with a thickness of 1.5 mm. and a fibre thickness of about 2μ is applied to the plastic strip 1 so that the free end of the covered coated fabric (3, 4, 5) still extends 6 mm. over the glass fiber fleece 2. This is then cut up into 6 mm. wide test strips.

When 15 μl. of whole blood B are now applied to a sample application zone 2a (see FIG. 1) of the glass fiber fleece 2, the plasma component of the blood penetrates through the whole glass fibre fleece within 30 to 60 seconds and is then, therefore, below the covered coated fabric (3, 4, 5), whereas the erythrocytes are held in the application zone 2a. By applying pressure to the transparent film 3 covering the coated fabric (3, 4), the reagent containing film layer 4 comes into contact with the separated plasma via the fabric layer 3 and is uniformly moistened through. The glucose contained in the plasma reacts with the reagent-containing film layer 4 within 1 to 2 minutes, depending upon its concentration, to develop a more or less deep blue coloration.

Figure 2:
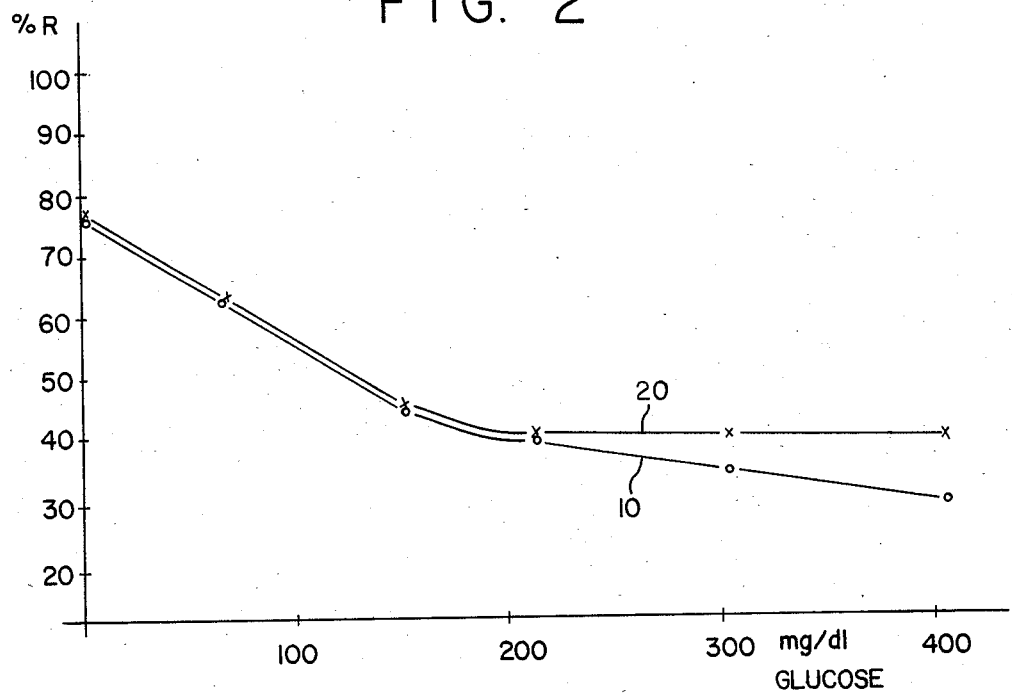
FIG. 2 is a nomograph comparison of the operation of the embodiment in FIG. 1 with a known embodiment.

The pressure for moistening the reagent-containing film layer 3 with the plasma is preferably applied with the measurement head of a remission photometer which descends onto the transparent covering film layer 3 after an incubation time for the plasma separation. After reaction times of 60 seconds, photometer measurements at a measurement wavelength of 630 nm yield the measurement curve 10 shown in FIG. 2. Curve 20 of FIG. 2 shows the measurement values obtained when the same reagent-containing film is applied to a film like the covering film layer 3 but now serving also as a carrier layer in the absence of a fabric layer on the other side of the reagent-containing film layer 4.

The difference between curve 10 (the invention) and curve 20 (prior art) clearly shows that differentiation amongst the highest glucose concentrations (200 to 400 mg/dl) is possible only with the construction according to the present invention. The stronger reagent reaction which the high-concentration differentiation indicates is possibly due to the supply of oxygen from the interior of the fabric, but was completely unexpected since a simple calculation shows that the oxygen originally present in the hollow spaces of the fabric layer 5 does not suffice by far for meeting the oxygen requirement of the reaction. Furthermore, the construction according to the present invention resulted in a marked reduction of the reaction time.

In contradistinction to the device described in Federal Republic of Germany Patent Specification No. 31 30 749, also, the transparent covering film layer 3 can be omitted since the reagent layer is sufficiently stabilised by the underlying fabric layer but it is preferably present in order to prevent a touching or damaging of the reagent containing layer 4.

EXAMPLE 2 SHOWN IN FIG. 3

Production of a test strip for the detection of glucose in urine

Figure 3:
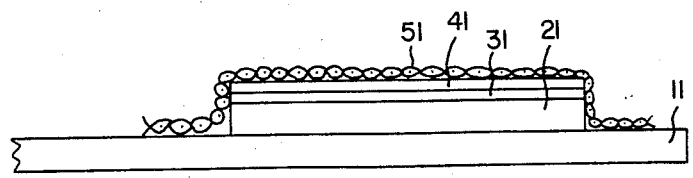
FIG. 3 is an elevation of another preferred embodiment.

20 KU glucose oxidase
80 KU peroxidase
5 ml. 1M citrate buffer, pH 5
0.13 g. sodium alginate
13 g. 50% polyvinyl propionate dispersion in water
0.375 g. 3,3',5,5'-tetramethylbenzidine
0.1 g. 1-phenylsemicarbazide
1 g. dioctyl sodium sulphosuccinate
5 ml. methoxyethanol
10 g. silica gel
12 ml. water are worked up to give a homogeneous mass, coated with a thickness of 0.1 mm. onto only one side of a 350μ thick polyester fleece (Dupont/Remey 2033) 31 and dried to form a reagent-containing film 41 embedded thereon. The so-obtained coated carrier 41 and 31 is, as described in Federal Republic of Germany Patent Specification No. 31 18 381, fixed over a slow-absorbing paper 21 on a synthetic resin film 11 serving as a handle with a covering thin fabric or mesh 51 which has been treated with a wetting agent and worked up to give test strips of the type illustrated in FIG. 3 of the accompanying drawings.

When the strips are dipped into glucose-containing urine samples, then, even in the case of careless handling, there are obtained reaction colours which are free from spots and of edge colorations.

EXAMPLE 3

Production of a test strip for the detection of cholesterol in blood 2.5 KU cholesterol oxidase
1.5 KU cholesterol esterase
50 KU peroxidase
10 mg. gallic acid
0.5 g. 3,3',5,5'-tetramethylbenzidine
0.3 g. dioctyl sodium sulphosuccinate
1.5 ml. acetone
6.5 g. 50% polyvinyl propionate dispersion in water
5 g. titanium dioxide
10 g. cellulose
15 ml. phosphate buffer 0.5M, pH 7
20 ml. water are worked up to give a homogeneous mass, coated with a thickness of 0.15 mm. onto a 200μ thick multifilar polyester fabric (2 F 777 Schweizer Seidengaze-Fabrik) and dried.

The coated carrier so obtained is, as described in Example 1, worked up to give test strips.

The reaction with cholesterol-containing blood took place as in Example 1 and, after a reaction time of 100 seconds, gave an excellent graduation over the whole relevant concentration range.

EXAMPLE 4

Production of a test strip for the detection of triglycerides in blood

50 KU peroxidase
20 KU cholesterol esterase
50 KU glycerol kinase
10 KU glycerophosphate oxidase
20 g. 50% polyvinyl propionate dispersion in water
20 g. cellulose
0.2 g. sodium alginate
10 g. titanium dioxide
0.68 g. 3,3',5,5'-tetramethylbenzidine
0.30 g. dioctyl sodium sulphosuccinate
1.5 ml. acetone
25 ml. 0.2M phosphate buffer, pH 7.8
10 ml. water
0.2 g. adenosine triphosphate are worked up to give a homogeneous mass and coated with a thickness of 0.2 mm. on a 210µ thick cotton fabric and dried. The so obtained coated carrier is, as described in Example 1, worked up to give test strips.

The reaction with triglyceride-containing blood took place as in Example 1 and gave, after a reaction time of 120 seconds, an excellent graduation over the whole relevant concentration range.

EXAMPLE 5

Production of a test strip for the detection of uric acid in blood

40 KU peroxidase
1 KU uricase
18 g. 50% polyvinyl propionate dispersion in water
0.25 g. sodium alginate
0.5 g. non-ionic wetting agent
0.5 g. disodium ethylenediamine-tetraacetic acid
20 g. kieselguhr
20 ml. 0.2M phosphate buffer, pH 7
0.4 g. primaquine diphosphate
18 ml. water are worked up to give a homogeneous mass and coated with a thickness of 0.2 mm. on to a 200µ thick multifilar polyester fabric (2 F 777 Schweizer Seidengaze-Fabrik) and dried.

A thin filter paper (597 NF-Ind., Schleicher & Schüll) is impregnated with 0.2 g. 4-aminoantipyrine and 0.2 g. non-ionic wetting agent in 50 ml. water and dried.

Test strips are produced as described in Example 1 which, between the separation fleece and the lower side of the reagent fabric, contained a layer of aminoantipyrine paper (not shown).

The reaction with uric acid-containing blood took place as in Example 1 and, after a reaction time of 120 seconds, gave an excellent graduation over the whole relevant concentration range.

EXAMPLE 6

Production of a test strip for the detection of γ-glutamyl transferase in blood 1.0 g. N-methylanthranilic acid
2.5 g. glycylglycine
0.85 g. disodium ethylenediamine-tetraacetic acid
0.2 g. glutamyl-p-phenylenediamine-3-carboxylic acid
20 g. 50% polyvinyl propionate dispersion in water
0.2 g. sodium alginate
0.35 g. dioctyl sodium sulphosuccinate
1.0 ml. methanol
5 g. titanium dioxide
8 g. cellulose
15 ml. tris buffer, pH 7.6
15 ml. water are worked up to give a homogeneous mass and coated with a thickness of 0.15 mm. on a 250 µm. thick multifilar polyamide fabric (1093 Verseidag-Industrie-Textilien GmbH) and dried.

A teabag paper of the firm Schöller & Hösch with a weight per unit surface area of 12 g./m² is impregnated with an aqueous solution containing 250 mmole/liter of potassium ferricyanide and dried for 5 minutes at 30° C. Test strips are produced as described in FIG. 1 of the accompanying drawings which, between the separation fleece and the lower side of the reagent fabric, additionally contained a layer of the oxidation paper (not shown).

The reaction with γ-glutamyl transferase-containing blood took place as in Example 1 and, after a reaction time of 120 seconds, gave an excellent graduation over the whole relevant concentration range.

EXAMPLE 7

Production of a test strip for the detection of bilirubin in blood 0.2 g. 2-methoxy-4-nitrobenzenediazonium tetrafluoroborate
1.5 g. metaphosphoric acid
1.5 g. diphenylphosphoric acid
0.2 g. dioctyl sodium sulphosuccinate
5 g. silica gel
1 g. cellulose
7.5 g. 40% polyvinylidene chloride dispersion (Diofan 217 D, BASF) in water
15 g. 2.5% swelling agent (Bentone EW, National Lead) in water are worked up to give a homogeneous mass and coated with a thickness of 0.2 mm. on a 200 µm. thick multifilar polyester fabric (2 F 777 Schweizer Seidengaze-Fabrik) and dried.

The so obtained coated carrier is worked up to give test strips as described in Example 1. The reaction with bilirubin-containing blood took place as in Example 1 and, after a reaction time of 60 seconds, gave an excellent graduation over the whole relevant concentration range.

EXAMPLE 8

Production of a test strip for the detection of uric acid in blood 8.4 g. gelatine
40 ml. phosphate buffer (0.5M, pH 7.0)
0.28 g. polyoxyethylene sorbitan oleate (Tween 20)
5 ml. enzyme suspension (0.5 KU uricase, 50 KU peroxidase in 5 ml. water)
0.15 g. indicator (2-(4-hydroxy-3,5-dimethoxyphenyl)-4,5-bis-(p-dimethylaminophenyl)-imidazole hydrochloride)
0.3 ml. isopropanol are worked up at 37° C. to give a homogeneous mass and applied by means of a 300 μm. nozzle in a curtain coating method, such as is usual in gelatine film technology, on to a multifilar polyamide fabric (Schweizer Seidengazefabrik 2F/131) and dried.

The reagent film so obtained is worked up as described in Example 1 to give test strips according to FIG. 1.

On application of 30 μl. blood at 37° C. to the area 2a and pressing the fabric layer (5) on to the transportation fleece (2), after 1 minute a blue coloration, which is proportional to the uric acid concentration, may be read off after another 1 to 2 minutes. Using a remission photometer, the values given in the following Table are read off at a wavelength of 680 nm.

TABLE

| uric acid mg./100 ml. | % remission |
| --- | --- |
| 0 | 66.4 |
| 5 | 46.7 |
| 15 | 33.4 |

It will be understood that the specification and examples are illustrative but not limitative of the present invention and that other embodiments within the spirit and scope of the invention will suggest themselves to those skilled in the art.

What is claimed is:

1. A test strip, comprising:

a carrier layer made of one of a multifilar fabric and fleece;

a dry, reagent-containing film layer coatingly embedded at least preponderantly on and into only one side of the carrier layer; and a synthetic resin film on the other side of the carrier layer from the preponderance of the reagent film layer.

2. The test strip of claim 1, wherein the reagent film layer has a thickness, when dry, of from about $15\mu$ to about $100\mu$.

3. The test strip of claim 1, and further comprising an absorbent layer between the carrier layer and the synthetic resin film.

4. The test strip of claim 3, wherein the reagent film layer has a thickness, when dry, of from about $15\mu$ to about $100\mu$.

5. The test strip of claim 3, and further comprising a thin mesh covering the reagent film layer and fixing the layers to the synthetic resin film.

6. The test strip of claim 5, wherein the reagent film layer has a thickness, when dry, of from about $15\mu$ to about $100\mu$.

7. The test strip of claim 3, and further comprising means fixing only one edge of the carrier layer to the synthetic resin film for bringing the reagent film layer into contact with liquid from the absorbent layer only by pressing the layers together.

8. The test strip of claim 7, wherein the reagent film layer has a thickness, when dry, of from about $15\mu$ to about $100\mu$.

9. The test strip of claim 7, and further comprising a covering film layer lying over the reagent film layer.

10. The test strip of claim 9, wherein the reagent film layer has a thickness, when dry, of from about $15\mu$ to about $100\mu$.

11. The test strip of claim 9, wherein the covering film layer is transparent and attached to the reagent film layer.

12. The test strip of claim 11, wherein the reagent film layer has a thickness, when dry, of from about $15\mu$ to about $100\mu$.

* * * * *